US012727962B2

(12) United States Patent
Joshi et al.

(10) Patent No.: US 12,727,962 B2
(45) Date of Patent: Sep. 8, 2026

(54) SYSTEM AND METHOD FOR IMAGE REGISTRATION

(71) Applicant: Erbe Vision GmbH, Wurmlingen (DE)

(72) Inventors: Shirish Joshi, Wurmlingen (DE); Faisal Kalim, Reutlingen (DE); Subhamoy Mandal, West Bengal (IN)

(73) Assignee: ERBE VISION GMBH, Wurmlingen (DE)

(*) Notice: Subject to any disclaimer, the term of this patent is extended or adjusted under 35 U.S.C. 154(b) by 0 days.

(21) Appl. No.: 17/971,220

(22) Filed: Oct. 21, 2022

(65) Prior Publication Data

US 2023/0131750 A1 Apr. 27, 2023

(30) Foreign Application Priority Data

Oct. 25, 2021 (EP) .................................... 21204574

(51) Int. Cl.
*A61B 90/00* (2016.01)
*G06T 7/11* (2017.01)
(Continued)

(52) U.S. Cl.
CPC ................ *A61B 90/37* (2016.02); *G06T 7/11* (2017.01); *G06T 7/33* (2017.01); *G06T 11/00* (2013.01);
(Continued)

(58) Field of Classification Search
CPC .............. A61B 90/37; A61B 2090/363; A61B 2090/365; A61B 2090/373; A61B 90/36;
(Continued)

(56) References Cited

U.S. PATENT DOCUMENTS 9,901,409 B2 2/2018 Yang et al.
9,968,285 B2 5/2018 Valsan et al.
(Continued)

FOREIGN PATENT DOCUMENTS

CN 1117707 A 2/1996
CN 101862205 A 10/2010
(Continued)

OTHER PUBLICATIONS

Luu et al. 2018 Phys. Med. Biol. 63: article 175005, 12 pages (Year: 2018).*

*Primary Examiner* — Keith M Raymond
(74) *Attorney, Agent, or Firm* — Blank Rome LLP

(57) ABSTRACT

Embodiments of the invention provide systems and methods for providing augmented reality to a surgeon with the steps of acquiring at least one preoperative medical scan image of a region of interest in which the surgery is to be performed and introducing a fiducial device non-invasively or minimal invasively into a body lumen present in the region of interest of a patient. The fiducial device will be in particular introduced into a lumen, which can be clearly identified in the medical scan image. The fiducial device is adapted to emit infrared light either by using infrared light source or by using fluorescent material placed in or in the fiducial device ad to be excited by illumination light or exciting light. After acquiring at least one imaging light live image and one infrared live image the tissue structure of the body lumen with the fiducial device placed therein is clearly detectable within the live image and can reliably registered and matched to the scan image for presenting the overlaid images and to the surgeon.

17 Claims, 4 Drawing Sheets

(51) Int. Cl.
*G06T 7/33* (2017.01)
*G06T 11/00* (2026.01)

(52) U.S. Cl.
CPC ... *A61B 2090/363* (2016.02); *A61B 2090/365* (2016.02); *A61B 2090/373* (2016.02); *G06T 2207/10048* (2013.01); *G06T 2207/10064* (2013.01); *G06T 2210/41* (2013.01)

(58) Field of Classification Search
CPC .............. A61B 90/30; A61B 2034/105; A61B 2034/2055; A61B 2090/3612; A61B 2090/3941; A61B 2090/3945; A61B 90/361; A61B 90/39; A61B 2090/306; A61B 2090/309; A61B 2090/3762; A61B 2090/3983; G06T 7/11; G06T 7/33; G06T 11/00; G06T 2207/10048; G06T 2207/10064; G06T 2210/41; G06T 7/62; G16H 30/20; G16H 30/40
See application file for complete search history.

(56) References Cited

U.S. PATENT DOCUMENTS

| | | | | |
|---|---|---|---|---|
| 2002/0099293 | A1 | 7/2002 | Fontenot et al. | |
| 2008/0183189 | A1* | 7/2008 | Teichman | A61B 6/506 606/130 |
| 2014/0073907 | A1* | 3/2014 | Kumar | A61B 10/0241 600/407 |
| 2018/0021102 | A1 | 1/2018 | Azizian et al. | |
| 2018/0153467 | A1* | 6/2018 | Lichtenstein | A61N 1/0551 |
| 2019/0001709 | A1 | 1/2019 | Yoda | |
| 2019/0059736 | A1 | 2/2019 | Maier-hein et al. | |
| 2019/0350671 | A1* | 11/2019 | Varshney | A61B 90/36 |
| 2019/0350672 | A1* | 11/2019 | Smith | A61L 31/14 |
| 2021/0015350 | A1* | 1/2021 | Butte | G02B 21/16 |

FOREIGN PATENT DOCUMENTS

| | | | | |
|---|---|---|---|---|
| CN | 103209656 A | | 7/2013 | |
| CN | 204909663 U | | 12/2015 | |
| CN | 107811705 A | | 3/2018 | |
| EP | 3 165 153 A1 | | 5/2017 | |
| EP | 3 398 169 A1 | | 11/2018 | |
| EP | 3 743 126 A1 | | 12/2020 | |
| WO | WO-2012033552 A1 | * | 3/2012 | A61B 1/00009 |
| WO | 2015135058 A1 | | 9/2015 | |
| WO | WO-2017114828 A1 | * | 7/2017 | A61B 1/00039 |
| WO | WO-2019145532 A1 | * | 8/2019 | A61L 31/10 |

* cited by examiner

SYSTEM AND METHOD FOR IMAGE REGISTRATION

CROSS-REFERENCE TO RELATED APPLICATION

This application claims priority to European Application No. 21204574.4, filed Oct. 25, 2021, the entirety of which is incorporated by reference herein.

TECHNICAL FIELD

Embodiments of the invention described herein relate to a system and a method for registration images captured during a preoperative scan and during surgery.

BACKGROUND

Registering medical scan images taken before surgery with the patient during surgery is a known problem. EP 3 398 169 A1 and WO 2017/114828 A1 disclose registration of a surgical image and an acquisition device like an endoscope using preoperative and live contour signatures of an anatomical object. A suitable processor compares the real time contour signature to the data base of preoperative contour signatures of the anatomical object to generate a group of potential contour signature matches for selecting of a final contour match. Registration of an image acquisition device to the surgical site is done based on an orientation corresponding to the selected final contour signature match.

US 2019/001709 A1 discloses an augmented reality system including glasses for the surgeon, which glasses comprise cameras for recording a real time image. A plurality of sensors is adapted to determine the place and orientation of the glasses in space. The glasses are further adapted to display image data for the surgeon, which image overlays the real image the surgeon sees through the glasses. The registration process registers the image data with the view axis of the surgeon and uses point matching, surface/object matching, palpation of anatomic landmarks, and processing of a single plane or multi plane intra operative imaging. The registered image data will be projected viewable by the user of the augmented reality system.

EP 3 743 126 A0 and WO 2019/145532 A1 disclose coating medical tools such as fiducials with a fluorescent polymeric coating film, which is visible in near infrared light.

Further prior art can be found in U.S. Pat. No. 9,901,409 B2 and US 2018/021102 A1.

While several prior art documents discussed above consider registration of real live images and preoperative scan images and presenting an overlay image to the surgeon, there is still need for more reliably doing so in particular when considering treatment of body portions, which are highly deformable or variable due to time or positioning of the patient or due to other internal or external influences.

SUMMARY

The inventive augmented reality systems is adapted to provide at least one preoperative medical scan image, at least one live image obtained with illumination light, and a live image obtained with infrared light. The illumination light may be visible light enabling direct view by a regular camera or directly by the surgeon. The illumination light, however, may at least partly be out of the range of visible lights. Preferably the imaging light is in the detecting range of a camera for acquiring the live image. The illumination light live image and the infrared light live image can be captured together in one common live image. So both can be acquired by two separate cameras or by one single camera, alternatively. The at least one live image and/or the at least one illumination light live image are preferably images that are acquired, processed, and/or displayed at least substantially in real-time (i.e. within a defined time span, such as less than 200 ms, less than 150 ms, less than 100 ms, less than 50 ms or less than 10 ms). Alternatively, the images may be displayed with a delay (e.g. more than 500 ms, more than 750 ms, more than 1 s, more than 5s, or more than 10 s) by buffering or intermediate storing of the images. The acquired images may for example be processed by pre-processing (e.g. increasing contrast of the image, lighting correction), edge filtering, segmentation and/or visualizing information in a false-colour representation.

The system involves at least one light source for illuminating the surgery site with imaging light. Moreover, the light source may be adapted for emitting excitation light. Excitation light may be in the range of visible light or even may be invisible light like ultraviolet or infrared light. The excitation light may for example comprise wavelengths that are larger than 500 nm or larger than 600 nm, e.g. ranging from 600 to 800 nm, 600 to 900 nm, or 650 to 1350 nm (i.e. the near-infrared (NIR) range). The excitation light may for example also comprise wavelengths that are at least 1400 nm, at least 3000 nm, at least 8000 or at least 15000 nm The image registering system is adapted to register the preoperative medical scan image and the illumination light live image by registering the preoperative medical scan image primarily with the infrared light live image. The fluorescent fiducials will be clearly seen in the infrared light live image, even if hidden behind layers of biological tissue. If the fluorescent fiducials are in the visible range, the fluorescent fiducials will be seen in the illumination light live image. Registering the preoperative scan image with no fiducials therein with the infrared light live image relies on structures of the tissue of the region of interest, in particular the structure of body lumens like the ureter, and the fiducial device placed therein. The registering system detects those tissue structures like the ureter or other tubular structures, vessels or hollow organs in the medical scan image. Later the surgeon places the fiducial device within the tubular structure (ureter) preferably in a non-invasive way. The excitation light and the visible and/or infrared light of the fluorescent material placed in or on the fiducial device both have wavelengths for which the biological tissue, and in particular blood, is transparent. The visible light of the fluorescent material may for example comprise wavelengths larger than 500 nm. The infrared light of the fluorescent material may for example comprise wavelengths that are larger than 600 nm, e.g. ranging from 600 to 800 nm, 600 to 900 nm, or 650 to 1350 nm (i.e. the near-infrared (NIR) range). The infrared light may for example also comprise wavelengths that are at least 1400 nm, at least 3000 nm, at least 8000 or at least 15000 nm. Transparent means in particular that the excitation light and the infrared light of the fluorescent material have a sufficiently high penetration depth and/or a sufficiently low absorption in biological tissue and/or blood. This light may for example travel through biological tissue and/or blood at least 1 mm, particularly at least 2 mm, more particularly at least 5 mm, preferably at least 8 mm, more preferably at least 10 mm. So this light easily travels through biological tissue and/or blood. The fluorescent fiducials will be clearly seen in the infrared light live image, even if hidden behind layers of biological tissue or obscured by blood or other body fluids. While the surgeon does not have direct view at the fiducials the image registering system will use the marks of the fiducial device for registering all three images (scan image, infrared live image, and illumination light live image).

Moreover the image registering system may be adapted to re-register the preoperative medical scan image and the illumination light live image already registered otherwise. The term re-registering designates a process during which an existing registration of the preoperative medical scan image and the illumination light live image is corrected or the registration made more precisely. This allows for taking care of deformations of the patient or tissue in the operation field. Those deformations may result from placing the patient in a position which is different from the position in which the medical scan image was taken. Deformations may further result from inflating the operation area e.g. during laparoscopy. Re-registering the medical scan image and the live image yield precise registration and hence better operation results. While the registering can be done before the surgery, e.g. based on an operation plan, the re-registering can be done during surgery.

The medical scan image can pre-operatively be taken by any medical imaging method as there are ultrasonic imaging, computer tomography, X-ray imaging, magnetic resonance imaging, positron emission tomography and many others.

The excitation light may be light within the wavelength range of visible light or outside that range. The light source may be adapted to emit both types of lights. It is also possible to use two distinct light sources, one for emitting illumination light and another one for emitting excitation light.

The live imaging device may be a camera adapted to detect both, imaging light back scattered from the tissue and visible and/or infrared light sent out by the fiducial device and shining through the tissue. Alternatively, distinct imaging devices may be used one for acquiring the illumination light live image and another one for acquiring the infrared light live image. Both imaging devices may be cameras or one single camera with constant or variable aperture angle. The camera(s) may have an objective with constant or variable focal distance. In any case, the infrared light image and the illumination light image will preferably be acquired with the same scale.

The fiducial device may have two or more areas with light emitting elements, which preferably consist of or comprise fluorescent material, preferably near infrared fluorescent material. The infrared emitting fluorescent material may be arranged in a known pattern and at spots with known distances one from another. So the fiducial device may be used as a reference standard.

The system may include a tracking system for determining the location and orientation of the fiducial device. Likewise the system may involve a tracking system for determining location and orientation of the camera, e.g. a laparoscopic camera by which the surgeon inspects the operation field. The fiducial device having two or more elements emitting infrared lights detectable by the infrared image acquiring camera indicates a scale of the live image (note that the illumination light image and the infrared light image are preferably taken with the same scale). So the surgeon may even take measurements in the illumination light image.

The registering system may rely on structures detected within the medical scan image and on the infrared light image only. Detectable structures are solid structures as there are bones, as well as soft tissue structures in particular hollow organs, tubular structures (e.g. the ureter), vessels or the like into which the fiducial device may be introduced in a non-invasive way. The fiducial device introduced into the hollow organ will make visible the specific tissue structure in the infrared light image and allow for registration with the medical scan image by scaling, rotating and shifting the images until they matchingly overlay.

Furthermore, the registration system may be adapted for detecting and correcting distortion of the tissue and warping thereof. In particular, local deformations may be present when comparing the medical scan image and the illumination light live image. This may be due to several factors as there is inflation of the body of the patient during laparoscopy, repositioning of the patient, physiological processes and the like. For compensating those deformations the registration system may first determine the deformations by determining the local distortions based on the positions of tissue structures in the medical scan image and the same structures re-found in the infrared light image. The fiducial device may be used for locating tissue structures in the infrared light live image, which structures will not be readily visible neither in the infrared light image nor in the illumination light image. So the fiducial device will be used as an indicator of tissue structures, which easily can be found in the medical scan image but are not very visible in the infrared light image or in the visible light image.

BRIEF DESCRIPTION OF THE DRAWINGS

Further details and advantages can be taken from the drawing and the embodiments of description and from claims as well. Embodiments of the invention are illustrated in the drawings in which

DETAILED DESCRIPTION

Figure 1:
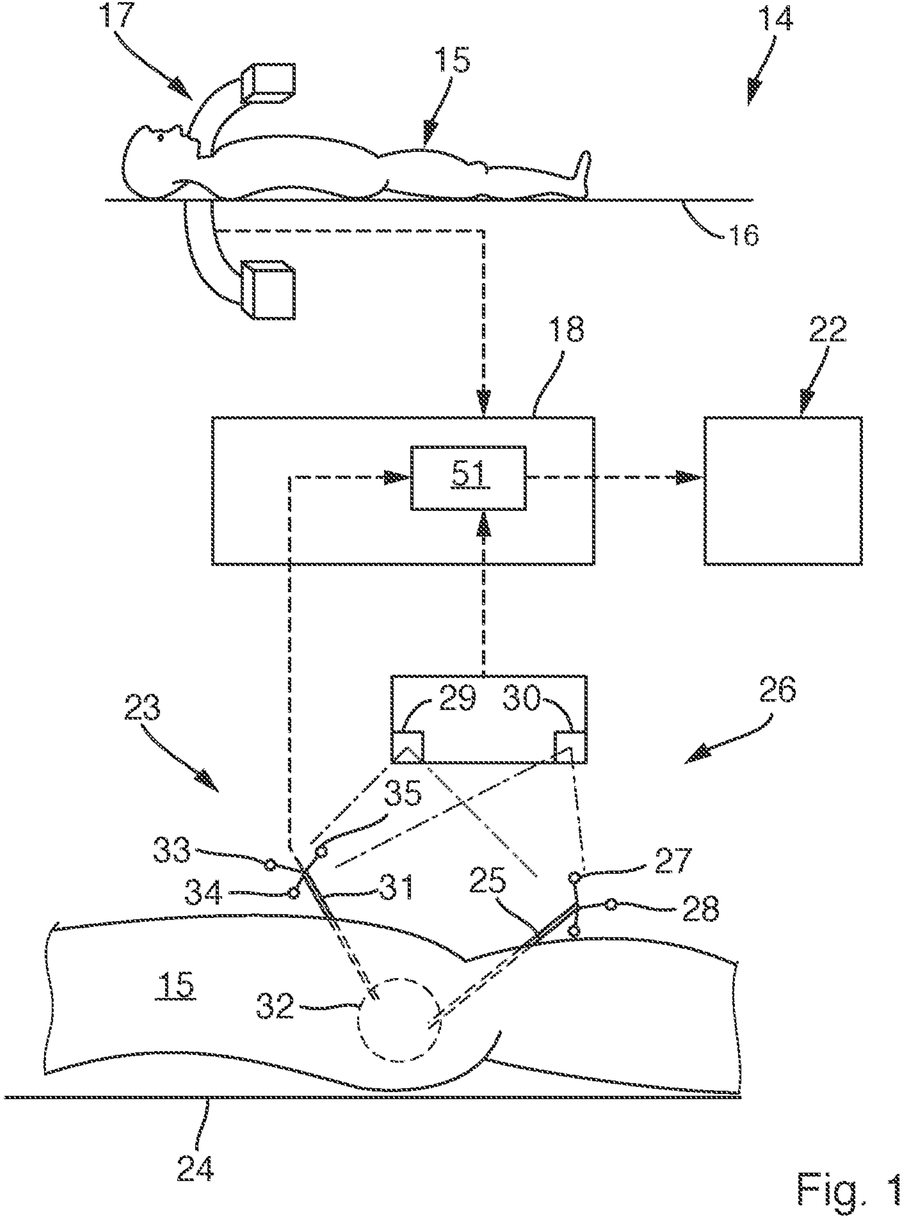
FIG. 1 illustrates the inventive system during medical scan of a patient and during surgery in a highly abstract way, FIG. 2 an illustration of a laparoscopic camera and tissue of the patient during surgery, FIG. 3 medical scan images taken during medical imaging, FIG. 4 an illumination light live image, FIG. 5 an infrared light live image, FIG. 6 a medical scan image of the same region of interest as illustrated in FIGS. 4 and 5, FIG. 7 an overlay image consisting of the illumination light image of FIG. 4 and the medical scan image of FIG. 6 registered along the infrared light image of FIG. 5, FIG. 8 an illumination light live image similar to FIG. 4, FIG. 9 an infrared light image of the operation site with a fiducial device introduced into a hollow organ present in the region of interest, FIG. 10 a medical scan image of the region of interest, FIG. 11 a distortion map obtained by comparing the infrared light image of FIG. 9 and the scan image of FIG. 10 and FIG. 12 an overlay image presented to the surgeon obtained by overlaying the visible light image of FIG. 8 with the scan image of FIG. 10 corrected along the distortion indicated in FIG. 11.

An augmented reality system 14 can be taken from FIG. 1, which illustrates a patient 15 resting on a table 16 during medical imaging. As a scan apparatus 17 for acquiring CT scans a C-arm is illustrated for illustration purposes only. It should be understood that any medical imaging system and any medical imaging method and modality may be used for acquiring preoperative medical scan images and supplying them to a processing system 18.

The processing system 18 may control any movement and activation or deactivation of the C-arm or any other scan apparatus 17. The processing system may be any type of computer or computer network or hard and/or software adapted to produce scan images from a medical scan.

Figure 3:
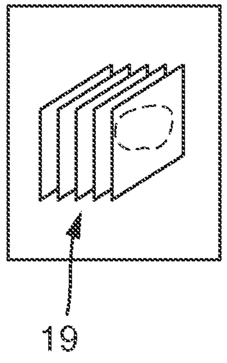
Figure 3:
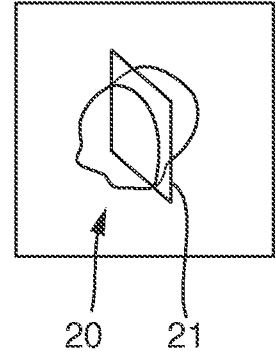
Figure 3:
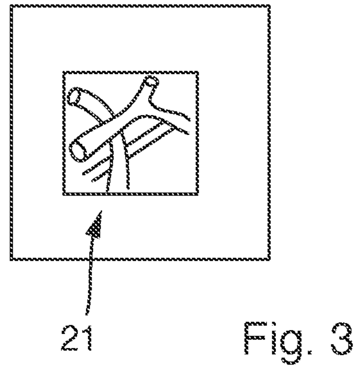

FIG. 3 illustrates the operation of the scan apparatus 17 together with the processing system 18. The scan apparatus 17 provides a number of scans e.g. CT scans 19. The processing unit 18 may determine a volume model 20 of the body portion of interest. Furthermore, the processing system 18 may provide one or several medical scan images 21 obtained by intersecting the volume model 20 in any desired plane. The medical scan image 21 may be displayed on an image reproduction device 22 (FIG. 1), which may be any type of screen, flat screen, stereoscopic screen, virtual reality glasses or the like.

The augmented reality system 14 further comprises an operation site 23 where the patient 15 can be placed on a suitable support 24 like a table, chair or any other type of support for having the patient 15 rest in a suitable position. The augmented reality system 14 further provides a preferably non-invasive fiducial device 25 adapted to be introduced into the patient's 15 body, preferably into a body lumen as there is the ureter. A tracking system 26 may allow for locating the fiducial device 25 relative to the patient 15 e.g. by triangulation. At least two position markers 27, 28 may be provided preferably at the proximal end of fiducial device 25 which are visible by the locating system 26. Cameras 29, 30 may locate the markers 27, 28 and hence the location and orientation of the fiducial device 25 by triangulation. It is noted that any other type of tracking systems may be used which is suited for determining location and orientation of the device 25 relative to the patient 15 and/or the support 24.

Furthermore, the augmented reality system 14 may comprise a live imaging device 31, which may be a laparoscopic camera, an endoscopic camera or any other camera system for providing live images from any region of interest 32 of the patient. The region of interest 32 is symbolized by a dotted line circle in FIG. 1 which is the region where the surgery is to be performed. Exactly that region has been imaged during the preoperative scan performed by the scan apparatus 17. The volume model 20 typically includes the region of interest 32. Normally the pre-operative scan is taken in a non-inflated state of the patient's body which will later be somewhat inflated with CO2 for laparoscopic surgery.

The laparoscopic camera or any other type of live imaging device 31 may be connected to the locating system 26 so that location and orientation of the live imaging device can be obtained e.g. by triangulation. The live imaging device 31 may be connected to at least two locating marks 33, 34, 35, which can be located by the cameras 29 and 30. However, it is noted that any other type of location system may equally work.

The locations and orientations of the fiducial device 25 and the live imaging device 31 determined by the locating system 26 will be supplied to the processing system 18 as well as will be the live images taken by the live imaging device 31.

Figure 2:
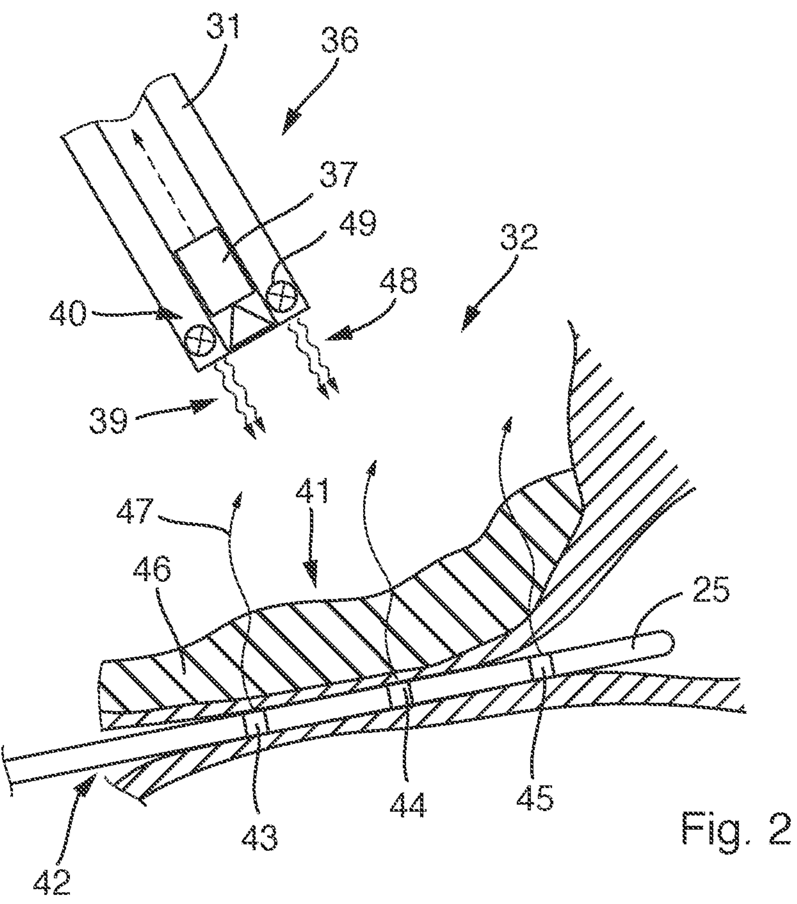

FIG. 2 illustrates the live imaging device 31 in a functional representation. The live imaging device 31 comprises a camera 37 for capturing a live image 38 (FIG. 4) generated with illumination light 39. A light source 40 may be provided for producing illumination light 39 and illuminating at least that portion of the region of interest 32 which is seen by the camera 37. The illumination light 39 may be visible light, e.g. white light. The light is in particular directed to a location 41 at which the surgery is to be performed and which is seen by the camera 37.

The surgery site 41 may include a body lumen, e.g. an ureter 42 in which the fiducial device 25 is placed. The fiducial device 25 may be a stiff or flexible rod or tube-like member having at least one preferably two or more marks 43 to 45, which are adapted to emit light capable of permeating biological tissue 46, in particular soft tissue like the wall of a tubular structure (e.g. the ureter) or a vessel, fat, muscles, fascia or the like. The at least one mark 43 (44, 45) may be punctiform, axially linear, ring shaped or the like.

The marks 43 to 45 are in particular adapted to emit infrared in particular near infrared light IR. The marks 43 to 45 may be illuminated by the fibre optics or LED members. Preferably, however, the marks 43 to 45 are passive light sources formed by fluorescent material producing infrared light. The infrared light preferably is near infrared light 47 emitted when excited by exciting light 48 sent out by a light source 49. The light source 48 may be identical with the light source 40 so that the exciting light 48 and the illumination light 39 are identical. However, it is likewise possible to use an exciting light source 49 different from the illumination light source 40. While the illumination light 39 may have a broad spectrum the exciting light source 49 may or may not be a narrow band source producing infrared light, visible light, or ultraviolet light depending on the type of fluorescent material present in the marks 43, 44, 45.

Figure 4:
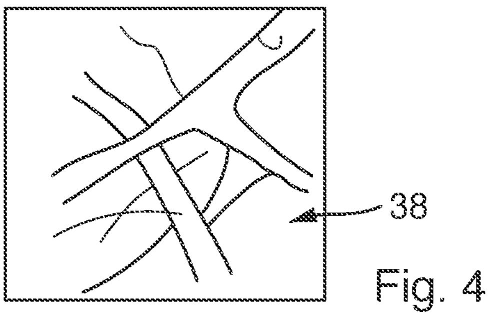
Figure 5:
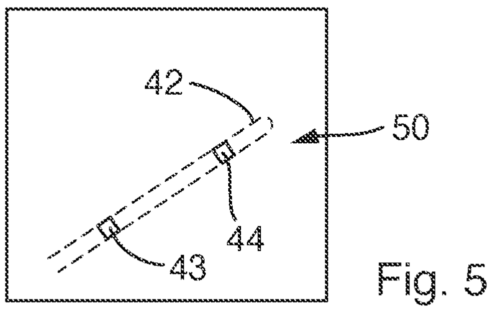
Figure 6:
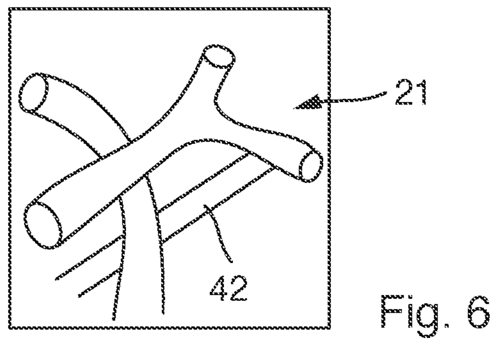

The camera 37 may acquire the live image 38 shown in FIG. 4 and an infrared light live image 50 illustrated in FIG. 5. The live images 38 and 50 may be captured together in one single image or separately.

The augmented reality system 14 comprises and image registering system 51, which may be part of the processing system 18. The registering system 51 may be or include a contour detector for detecting at least one soft tissue contour. Such a contour may be a vessel or any other hollow organ or tubular structure (e.g. the ureter) or the surface of an organ.

Figure 7:
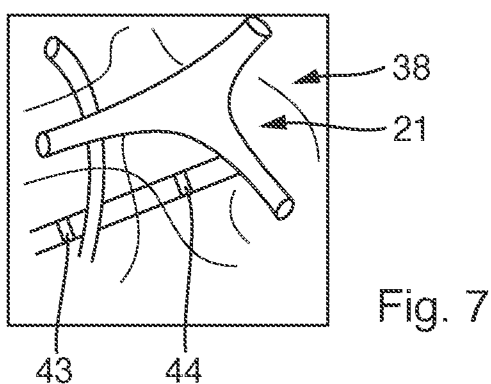

The image registering system is adapted to register at least one preoperative medical scan image 21 and the illumination light live image 38. For doing so, the image registering system 51 uses the infrared light live image 50 and in particular the at least two marks 43, 44, which are placed within the ureter 42 illustrated in FIG. 5 in dotted lines. While the ureter 42 is a tissue structure clearly identifiable and clearly identified in the medical scan image 21, the ureter may not be so visible in the illumination light image 38. However, by placing the fiducial 25 in the ureter 42, the marks 43 and 44 will indicate where the ureter is in the live image 38 so that the image registering system 51 can now reliably and precisely register the medical scan image 21 to the illumination light image 38 (and the infrared light image 50 as well). After registering the illumination light live image 38 together with the scan image 21 (and if desired the infrared light image 59 may be displayed on the image reproduction device 22 as an overlay as illustrated in FIG. 7.

In doing so, the locating system 26 will always determine location and orientation of both, the fiducial device 25 and the live imaging device 31 which provides the illumination light image 38 and the infrared light image 50 together or separately. The processing system 18 will use the volume model 20 and find the scan image 21 at a plane, which is defined by the orientation of the live imaging device 31. The scan image 21 may include colours or graphics enhancing tissue structures for making visible different tissues like parenchyma tissue or tubular structures (e.g. the ureter) or vessels or the like. The system is in particular helpful if surgery in a distance of solid body portions like bones is performed. Organs of the patient may move due to relocation of the patient, due to relaxation, or due to inflation of the surgery site during laparoscopy. Using hollow organs for preferably non-invasively placing the fiducial device 25 therein, will help to avoid misalignment of the scan image 21 and the live image 38, which otherwise, could occur when only relying on bones or other body structures which soft tissue may move relative to.

Figure 8:
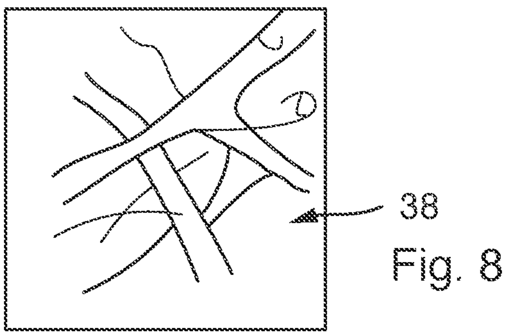
Figure 9:
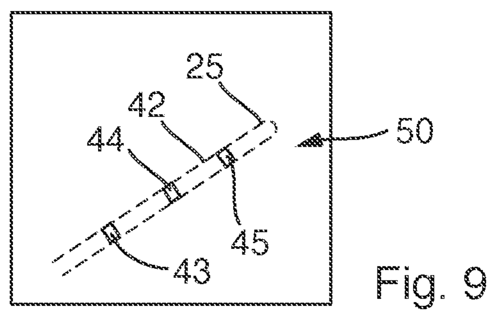
Figure 10:
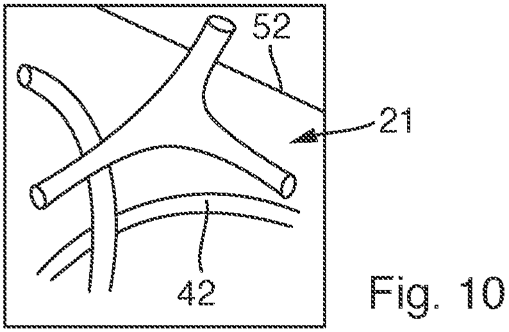
Figure 11:
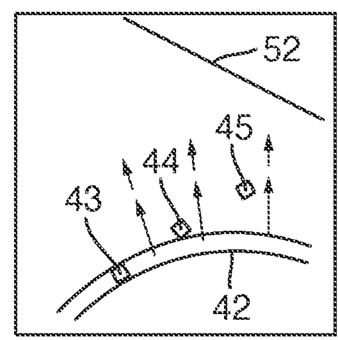
Figure 12:
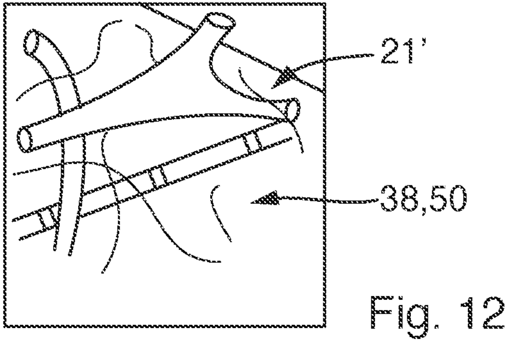

Embodiments of the invention pave the way for further improvements:

As mentioned above soft tissue of the patient may undergo heavy deformations between medical imaging and surgery. Even the introduction of the fiducial devise 25 into the ureter 42 or any other body lumen as well as inflating the internal body cavities for laparoscopic surgery may deform tissue structures. Embodiments allow for adapting the medical scan image 21 similar or even the same way as the real body was deformed so that the deformed scan image can better be registered with the real live image. This process is to be performed by the processing system 18 and illustrated in FIGS. 8 to 12. The illumination light live image 38 is illustrated in FIG. 8. So is the infrared light image 50 illustrated in FIG. 9. As can be seen, the ureter 42 is straight so that the three marks 43 to 45 emitting infrared light are arranged in a straight line. Obviously, the patient's body is deformed since the medical scan image 21 includes the ureter 42 curved. Furthermore, the scan image 21 includes a solid body structure like a bone 52, which of course may not be deformed at all. So clearly there will always be some degree of misalignment no matter how one tries to register the illumination light live image 38 and the scan image 21. The processing system in particular, the image registering system 51 (which includes a contour detector) may now distort the medical scan image 21 the same way as the live image 38 is distorted relative to the (non-distorted) medical scan image 21. For doing so, the image registering system 51 now identifies the tissue structure the fiducial device 25 is placed in e.g. the ureter 42. In addition, it may identify natural solid body structures as bone 52. While the bone 52 can be seen as being non-distorted it can be seen that distortion of the scan image is necessary for bringing the scan image ureter 42 in registration with the three marks 43, 44, 45 of the infrared image 50 as illustrated in FIG. 11. Small arrows symbolize the degree of distortion of the scan image, which is necessary for bringing the medical scan image 21 into registration with the live images 38 and 50. The result can be seen from FIG. 12 which illustrates the distorted medical scan image 21' in registration with the live images 38, 50.

Embodiments of the invention overcome formerly present difficulties and reliability issues of patent registration in laparoscopic surgeries and allows for augmented reality assistance. Embodiments provide a novel method of patient 15 registration using an infrared camera and a fiducial device 25 to be introduced in a body lumen like the ureter or another body orifice. The fiducial device 25 comprise fiducial markers 43 to 45. An embodiment of the invention reduces the number and complexity of planning work flow steps and also reduces or even eliminates the need of additional invasive procedures. Further the method allows for changing the patient's positions during surgery with minimal or no hindrances to the surgical procedures. The method does not require additional radiological imaging procedures included into the work flow.

The inventive method in particular allows for registration of preoperative scans taken with a "not deformed" patient body with a "heavily deformed" patient body as for example after insulation with CO2 gas for allowing laparoscopic surgery. Because of the deformation a preoperative scan image is no longer identical with an intraoperative medical scan image. Embodiments allow for compensating these deformations and removes the necessity of intraoperative scan imaging. This contributes to the patient's safety dramatically reduces the operation time and to some extent makes possible those surgery at all.

Embodiments provide systems and methods for providing augmented reality to a surgeon with the steps of acquiring at least one preoperative medical scan image of a region of interest in which the surgery is to be performed and introducing a fiducial device 25 non-invasively or minimal invasively into a body lumen present in the region of interest of a patient. The fiducial device will be in particular introduced into a lumen, which can be clearly identified in the medical scan image. The fiducial device 25 is adapted to emit infrared light either by using infrared light source or by using fluorescent material placed in or on the fiducial device and to be excited by illumination light 39 or exciting light 48. After acquiring at least one imaging light live image and one infrared live image the tissue structure of the body lumen with the fiducial device 25 placed therein is clearly detectable within the live image 38 and can reliably registered and matched to the scan image 21 for presenting the overlaid images 21 and 38 to the surgeon.

The invention claimed is:

1. An augmented reality system comprising:

a scan apparatus adapted to provide at least one scan image of a region of interest of a patient in which a surgery is to be performed, wherein a body lumen that is present in the region of interest of the patient is visible in the at least one scan image;

a fiducial device adapted to be introduced into the body lumen present in the region of interest of the patient, the fiducial device providing at least two fiducial marks adapted to emit infrared light and/or visible light capable of permeating biological tissue, the at least two fiducial marks being arranged in a known pattern on the fiducial device, the fiducial device including at least two position markers being visible to a locating system;

a light source adapted to illuminate the region of interest with illumination light, where the surgery is to be performed;

a live imaging device adapted to acquire at least one illumination light live image and at least one infrared light live image of the region of interest including the known pattern of the at least two fiducial marks, the live imaging device including at least two locating marks;

the locating system being configured to determine a location and an orientation of the fiducial device by triangulation of the at least two position markers and to determine a location and an orientation of the live imaging device by triangulation of the at least two locating marks;

a processing system configured to determine a three-dimensional volume model of the region of interest based on the at least one scan image, and provide at least one pre-operative medical scan image by intersecting the volume model with a plane based on the orientation of the live imaging device;

an image registering system adapted to register or re-register the at least one pre-operative medical scan image with the at least one infrared light live image and the at least one illumination light live image using the known pattern of the at least two fiducial marks provided by the fiducial device, thereby creating an overlay image of the at least one pre-operative medical scan image registered with the at least one infrared light live image and the at least one illumination light live image, wherein the body lumen is visible in the overlay image, the image registering system adapted to detect a contour of the body lumen adapted to receive the fiducial device in the at least one pre-operative medical scan image, the image registering system further adapted to determine distortions between the body lumen of the at least one pre-operative medical scan and the known pattern of the at least two fiducial marks of the infrared light live image and to create a distorted pre-operative medical scan image by distorting the at least one pre-operative medical scan based on the determined distortions, thereby bringing the contour of the body lumen of the at least one pre-operative medical scan into registration with the known pattern of the at least two fiducial markers of the infrared light like image; and an image reproduction device adapted to reproduce the overlay image.

2. The augmented reality system according to claim 1, wherein the at least two fiducial marks of the fiducial device are near-infrared fluorescent material placed in a distance one from another.

3. The augmented reality system according to claim 1, wherein a body of the fiducial device is a tube or rod-like element.

4. The augmented reality system according to claim 1, wherein the image registering system comprises a contour detector adapted to identify anatomic structures in the at least one pre-operative medical scan image.

5. The augmented reality system according to claim 1, wherein the image registering system comprises a contour detector a adapted to detect a contour of a solid body structure in the pre-operative medical scan image and the at least one infrared light live image and to determine distortions between the solid body structure of the pre-operative medical scan image and the at least one infrared light live image.

6. The augmented reality system according to claim 1, wherein the illumination light is visible light.

7. The augmented reality system according to claim 2, wherein the light source is adapted to emit excitation light adapted to cause the fluorescent material to emit infrared or near-infrared light.

8. The augmented reality system according to claim 1, wherein the image registering system is adapted to determine an image scale of the at least one illumination light live image and enhance or reduce the at least one pre-operative medical scan image to the same scale.

9. The augmented reality system according to claim 8, wherein the at least two fiducial marks of the fiducial device are near-infrared fluorescent material placed in a distance one from another, and wherein the image scale is defined by the distance.

10. The augmented reality system according to claim 1, wherein the image registering system is adapted to determine the distortions by comparing a shape and position of the body lumen in the at least one pre-operative medical scan image with a shape and position of the fiducial device in the at least one infrared light live image.

11. The augmented reality system according to claim 1, wherein the live imaging device is connected to a position locating system.

12. The augmented reality system according to claim 1, wherein the fiducial device is connected to a position locating system.

13. A method for providing augmented reality to a surgeon, comprising the steps of:

acquiring at least one scan image of a region of interest of a patient in which a surgery is to be performed, wherein a body lumen that is present in the region of interest of the patient is visible in the at least scan image;

introducing a fiducial device into the body lumen present in the region of interest of the patient, the fiducial device providing at least two fiducial markers adapted to emit infrared light and/or visible light capable of permeating biological tissue, the at least two fiducial marks being arranged in a known patter on the fiducial device, the fiducial device including at least two position markers;

illuminating the region of interest where the surgery is to be performed, with illumination light and exciting light;

acquiring at least one illumination light live image and at least one infrared light live image via a live imaging device, the infrared light live image including the known pattern of the at least two fiducial marks, the live imaging device including at least two locating marks;

determining a location and an orientation of the fiducial device by triangulating the at least two position markers and to determining a location and an orientation of the live imaging device by triangulating the at least two locating marks;

determining a three-dimensional volume model of the region of interest based on the at least one scan image, and providing at least one pre-operative medical scan image by intersecting the volume model with a plane based on the orientation of the live imaging device;

registering the at least one pre-operative medical scan image with the at least one infrared light live image and the at least one illumination light live image using the known pattern of the at least two fiducial marks provided by the fiducial device, thereby creating an overlay image of the at least one pre-operative medical scan image registered with the at least one infrared light live image and the at least one illumination light live image, wherein the body lumen is visible in the overlay image and reproducing the overlay image;

detecting a contour of the body lumen in the at least one pre-operative medical scan image;

determining distortions between the body lumen of the at least one pre-operative medical scan and the known patter of the at least two fiducial marks of the infrared light live image; and creating a distorted pre-operative medical scan image by distorting the at least one pre-operative medical scan based on the determined distortions, thereby bringing the contour of the body lumen of the at least one pre-operative medical scan into registration with the known pattern of the at least two fiducial marks of the infrared light like image.

14. The augmented reality system according to claim 1, wherein the body lumen is a ureter.

15. The method accordingly to claim 13, wherein the body lumen is a ureter.

16. The augmented reality system according to claim 3, wherein the body of the fiducial device is flexible.

17. The augmented reality system according to claim 3, wherein the body of the fiducial device is stiff.

* * * * *